US008965483B2

(12) United States Patent
Couture et al.

(10) Patent No.: US 8,965,483 B2
(45) Date of Patent: Feb. 24, 2015

(54) CAS SYSTEM FOR CONDYLE MEASUREMENT

(76) Inventors: Pierre Couture, Montréal (CA); Alain Richard, Lachine (CA); Louis-Philippe Amiot, Hampstead (CA)

(*) Notice: Subject to any disclaimer, the term of this patent is extended or adjusted under 35 U.S.C. 154(b) by 490 days.

(21) Appl. No.: 13/234,227

(22) Filed: Sep. 16, 2011

(65) Prior Publication Data

US 2012/0010500 A1 Jan. 12, 2012

Related U.S. Application Data

(62) Division of application No. 11/627,109, filed on Jan. 25, 2007, now Pat. No. 8,038,683.

(60) Provisional application No. 60/761,767, filed on Jan. 25, 2006.

(51) Int. Cl.
| | | |
|---|---|---|
| *A61B 5/05* | (2006.01) | |
| *A61B 6/00* | (2006.01) | |
| *A61B 5/107* | (2006.01) | |
| *A61B 8/00* | (2006.01) | |
| *A61B 17/15* | (2006.01) | |
| *A61B 19/00* | (2006.01) | |

(52) U.S. Cl.
CPC ............ *A61B 17/155* (2013.01); *A61B 19/203* (2013.01); *A61B 19/52* (2013.01); *A61B 19/5244* (2013.01); *A61B 2019/505* (2013.01); *A61B 2019/5255* (2013.01); *A61B 2019/5268* (2013.01); *A61B 2019/5289* (2013.01); *A61B 2019/5483* (2013.01); *A61B 2019/566* (2013.01)
USPC .......................................... 600/424; 600/587

(58) Field of Classification Search
CPC ............ A61B 5/05; A61B 6/00; A61B 5/107; A61B 8/00
USPC ................ 600/407, 426, 427, 587; 606/86 R, 606/87–89
See application file for complete search history.

(56) References Cited

U.S. PATENT DOCUMENTS

| 5,540,696 A | 7/1996 | Booth, Jr. |
| 5,624,444 A | 4/1997 | Wixon |

(Continued)

FOREIGN PATENT DOCUMENTS

WO 2006133573 12/2006

OTHER PUBLICATIONS

International Search Report of Application PCT/CA2007/000108.
(Continued)

*Primary Examiner* — Christopher Beccia
(74) *Attorney, Agent, or Firm* — Norton Rose Fulbright Canada LLP (57) ABSTRACT

A computer assisted surgery system for conducting orthopedic surgery on a knee joint includes a condyle digitizer having a posterior condyle abutment surface defining a first plane and a distal condyle abutment surface defining a second plane perpendicular to the first plane, and a trackable member which is locatable and trackable in three dimensional space by the computer assisted surgery system to define at least orientation of the condyle digitizer in real time. A computer determines a most remote reference point of the femur of the knee joint lying within at least one of the first and second planes when the condyle digitizer is abutted against condyles of the femur such that the posterior condyle abutment surface abuts a posterior side of the condyles and the distal condyle abutment surface abuts a distal side of the condyles.

16 Claims, 6 Drawing Sheets

(56) References Cited

U.S. PATENT DOCUMENTS 6,173,200 B1 * 1/2001 Cooke et al. .................. 600/425
7,104,997 B2 * 9/2006 Lionberger et al. ............. 606/88
2005/0190380 A1 * 9/2005 Plassky et al. ................ 356/614

OTHER PUBLICATIONS

Election/Restrictions Requirement Office Action dated Mar. 5, 2010.
Non-Final Office Action dated Jun. 10, 2010.
Final Office Action dated Oct. 27, 2010.

* cited by examiner

CAS SYSTEM FOR CONDYLE MEASUREMENT

CROSS-REFERENCE TO RELATED APPLICATIONS

The present application is a divisional of U.S. patent application Ser. No. 11/627,109 filed Jan. 25, 2007, now U.S. Pat. No. 8,038,683 which claims priority on U.S. Provisional Patent Application No. 60/761,767 filed Jan. 25, 2006, the entire contents of both of which is incorporated herein by reference.

TECHNICAL FIELD

The present invention relates generally to a Computer Assisted Surgery (CAS) system for use in orthopedic knee surgery, and more particularly to a CAS system, as well as an associated device and method, for measuring a femoral condyle during such a surgery.

BACKGROUND OF THE INVENTION

The use of Computer Assisted Surgery (CAS) systems for orthopedic operations in general, and for Total Knee Replacement (TKR) surgery in particular, is becoming increasingly more commonplace with advancements in CAS systems and equipment that ensure improved accuracy, fail safe operation and increasing ease of use.

During TKR surgery, the accuracy of cuts made in the patient's bone prior to the installation of any implant, and particularly the resection cut made in the condyles at the distal end of the femur, is important and contributes significantly to the success of the total knee replacement.

TKR surgery requires several precise cuts to be made in the femur and tibia, including the femoral condyle distal resection cut mentioned above, such that the implant fits correctly and best replicates the geometry of a natural healthy knee. Generally, in TKR surgery, the distal ends of both the femur and tibia are completely resected such that these joint articulation surfaces can be replaced with prosthetic implants. To perform these resection cuts, in both conventional and CAS TKR, it is well known to use a cutting guide which assists the surgeon such that he or she can make the resection cuts in the right position and orientation to ensure that the geometry of the knee, once reconstructed with the prosthetic implants, approaches as much as possible that of a healthy knee. In many conventional, i.e. non computer assisted, total knee replacement surgery a distal cutting block is positioned and aligned by the surgeon and pinned in place (typically on the anterior surface of the femur) such that the cutting slot is aligned in the correct location for the distal cut. In many CAS total knee replacement surgeries, it is also known to use a distal pin drill guide to accurately create the pin holes into which locating pins are inserted and employed to fix the distal cutting guide, either integrally formed with the distal pin drill guide or being a separate element, in the correct location to make the distal cut in the femoral condyles. Generally, the distal drill/cutting guide member comprises part of an assembly including an anterior guiding platform, that is fixed relative to the femur and on which the drill/cutting guide is displaceable by a selected, measurable amount to locate the drill/cutting guide in a predetermined position relative to the anterior guiding platform and therefore relative to the distal end of the femur. A tracked guide block is often intramedullarly fastened to the femur, and the anterior guiding platform can then be engaged thereto. Depending on the type of implant being used, and once aligned with the most distal femoral condyle, the drill/cutting guide can then be proximally displaced on the fixed anterior guiding platform by a selected amount corresponding to the amount of bone to be resected.

However, as TKR CAS techniques have developed, a large guide block which actually abuts the distal end of the femoral condyles is now less commonly used, and therefore alternate means are required to determine the exact location of the most distal point(s) on the femoral condyles, such that this can be used as a reference point from which the predetermined resection distance can be measured, calculated or otherwise determine, either by the surgeon and/or by the CAS system. Therefore, it is important to the success of the TKR procedure to be able to accurately determine the exact location of the most distal point on the femoral condyles, such that the distal resection distance can be accurately measured from this point.

The distal surfaces of the femoral condyles have been more recently located by CAS systems by using a digitizing pointer, which is calibrated and tracked in space by the CAS system and which is used to digitize a plurality of points on the surfaces of the condyles. The CAS system then uses these points, which are assumed to be representative of the distal condyle surfaces, to plot the condyle surfaces and thus determine the location of the most distal point thereof.

Several disadvantages exist with this method of determining the distal surface in general, and the most distal point thereon in particular. For example, such digitizing pointers typically have a relatively sharply pointed tip which can unintentionally penetrate a soft or damaged bone surface or any soft tissue or cartilage which may be present on the bone surface, depending on the amount of pressure exerted by the surgeon. While such measurement inaccuracies can be very small (such as 1 mm or less for example), these can nonetheless lead to significant differences between the actual distal surface of the condyles and that determined by the CAS system, resulting in improperly located distal resection cuts and thus proper fit of the implant. Additionally, while several points are taken on the distal condyle surfaces in order for the CAS system to digitize these surfaces, if the points chosen are not representative of the entire surface of if they are localized in one portion of the bone, errors in the resultant digitized surface can result. Determining by eye which portions of the condyle may be the most distal points, such that they can be digitized using the pointer, can also be particularly difficult on severely deformed or damaged bones.

Therefore, there is a need to provide a CAS system and device which enables a more accurate and simplified measurement of the most distal point(s) on the condyles of a femur prior to knee surgery.

SUMMARY OF THE INVENTION

It is accordingly an object of the present invention to provide an improved CAS system, and method using such a system, capable of determining more accurately the location of a most remote reference point, such as a most-distal point for example, on a femoral condyle during orthopedic knee surgery.

Therefore, in accordance with the present invention, there is provided a method of determining a reference point on condyles of a femur using a computer assisted surgery system, the method comprising: providing a digitizer having a trackable member which is locatable and trackable in three dimensional space by the computer assisted surgery system, the digitizer including perpendicular first and second planar surfaces; creating a digitized plane using the digitizer, the digitized plane being at least one of a posterior plane and a distal plane of the condyles, the posterior plane and the distal plane being respectively defined by said first planar surface and said second planar surface of the digitizer; and determining a location of the reference point in the digitized plane using the computer assisted surgical system, the reference point being a most remote point of the femur within said digitized plane.

There is also provided, in accordance with the present invention, a computer assisted surgery system for conducting orthopedic surgery on a knee joint, the knee joint including a femur defining a longitudinal mechanical axis and having condyles on the distal end thereof, the system comprising: a condyle digitizer including a posterior condyle abutment surface defining a first plane and a distal condyle abutment surface defining a second plane perpendicular to said first plane, and a trackable member which is locatable and trackable in three dimensional space by the computer assisted surgery system, thereby defining position and orientation of the condyle digitizer in real time; and a computer which determines a most remote reference point of the femur lying within at least one of said first and second planes when said condyle digitizer is abutted against the condyles of the femur such that the posterior condyle abutment surface abuts a posterior side of the condyles and the distal condyle abutment surface abuts a distal side of the condyles.

There is further provided, in accordance with the present invention, a computer assisted surgery system for orthopedic knee surgery comprising: a digitizer having first and second planar surfaces respectively abuttable against posterior and distal surfaces of condyles of a femur; means for determining the position and orientation of said first and second planar surfaces relative to the femur; and means for determining the location of a reference point in a digitized plane defined at least one of said first and second planar surfaces when abutted against the respective proximal and distal surfaces of the condyles, said reference point being a most remote point of the femur within said digitized plane.

BRIEF DESCRIPTION OF THE DRAWINGS

Further features and advantages of the present invention will become apparent from the following detailed description, taken in combination with the appended drawings, in which:

FIG. 2b is a lateral side view of the femur of FIG. 2a;

FIG. 5 is a lateral side view of a femur, such as that of FIG. 2a; and

DETAILED DESCRIPTION OF THE PREFERRED EMBODIMENT

Figure 1:
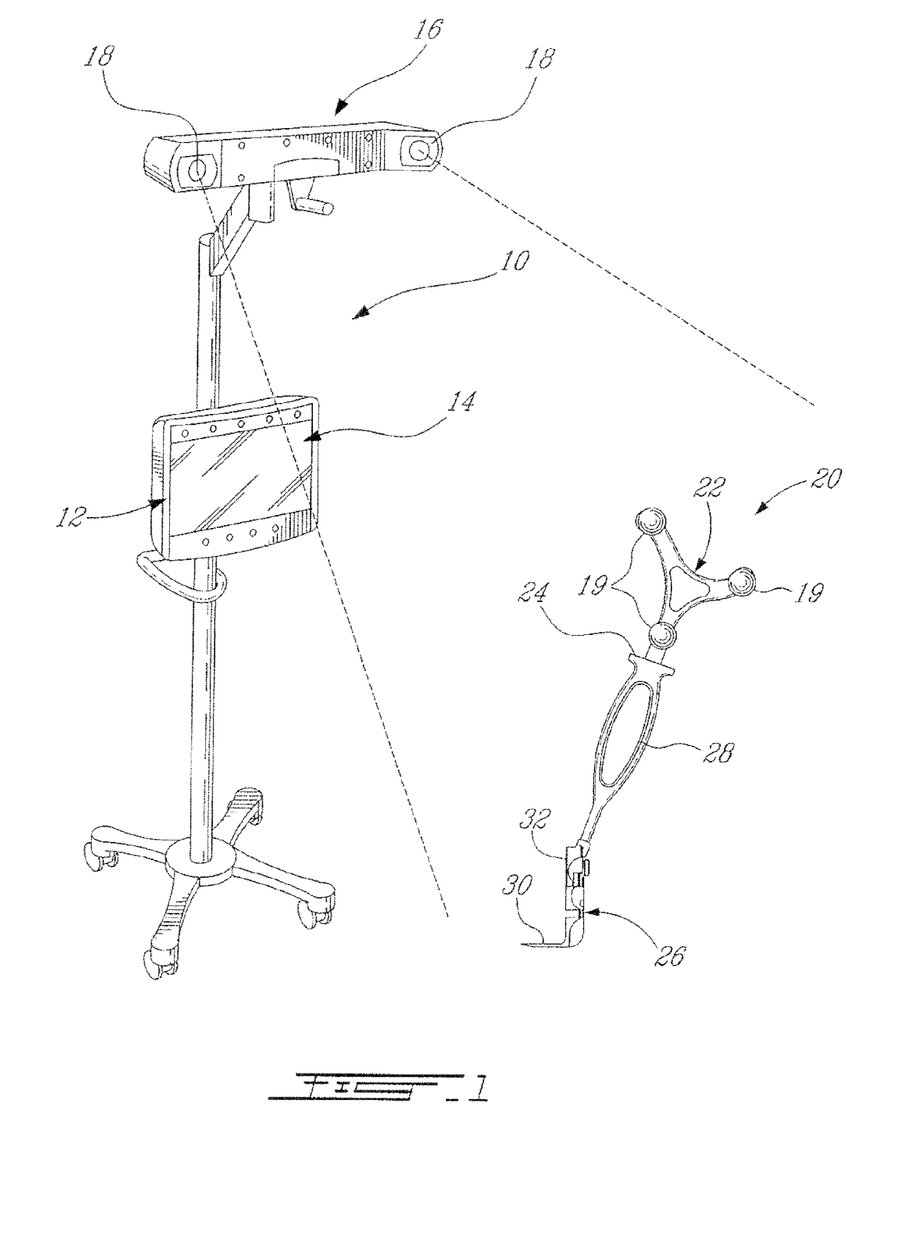
FIG. 1 is a perspective view of a condyle digitizer and Computer Assisted Surgery (CAS) system according to the present invention.

Referring to FIG. 1, the computer assisted surgery (CAS) system 10 is used for orthopedic surgery, and in the present embodiment the system is particularly employed for conducting total knee replacement (TKR) surgery. The CAS system 10 is capable of real time location and tracking of a plurality of trackable members in a surgical field, each having a distinctive set of identifiable markers thereon. These trackable members are thus affixed both to the surgical tools employed with the system 10 and to the bone elements undergoing surgery.

The CAS system 10 generally includes at least a computer 12, a display device 14 in communication with the computer, and a tracking system 16 also in communication with the computer. The tracking system 16 is preferably an optical tracking system, using infra-red cameras 18, however any other type of tracking system can also be used, such as one based on laser, ultrasound, electromagnetic or RF waves to locate the position of the identifiable markers of tracking members within range of the sensing devices of the system.

The CAS system 10 is capable of depicting the digitizer 20, as well as any other surgical tools, on the display device 14 (which may include a monitor for example) relative to the patient anatomy, including the pertinent bones which are also tracked in real time by the system. The CAS system 10 is preferably a CT-less system.

The CAS system 10 includes a digitizer tool 20 which is used in conjunction therewith, the digitizer 20 including a tracking member 22 having retro-reflective identifiable markers 19 thereon such that the tracking member 22 is locatable and trackable by the tracking system 16 of the CAS system 10, permitting the CAS system 10 such to determine the position, orientation and movement of the tracking member 22 (and therefore also the digitizer 20 to which it is fastened) in three dimensional space and in real time. The retro-reflective identifiable markers 19 of the trackable member 22 can be removably engaged to either side or both sides of the tracking member 22 of the digitizer 20, such that the best visual contact between the detectable markers 19 and the cameras 18 of the CAS system 10 is ensured. Therefore, regardless of which knee is being operated on the tracking member 22 will be readily visible and detected by the tracking system.

The digitizer 20 includes generally a first end 24 to which the tracking member 22 is engaged and an opposed second end 26. Between the first and second ends 24 and 26 is a handle portion 28 which is adapted to be grasped by the user in order to be able to manipulate the digitizer 20. The second end 26 of the digitizer includes a first condyle abutment surface 30 and a second condyle abutment surface 32. In the preferred embodiment, both condyle abutment surfaces are planar and perpendicularly arranged relative to each other. Thus, the first condyle abutment surface 30 defines a first plane and the second condyle abutment surface 32 defines a second plane which is substantially perpendicular to the first plane. In the embodiment depicted (see FIG. 3) and described in further detail herein, the first condyle abutment surface 30 is used to abut the posterior surfaces of the femoral condyles and the second condyle abutment surface 32 is used to abut the distal surfaces of the femoral condyles, and thus the first and second condyle abutment surfaces are said to be a posterior condyle abutment surface and a distal condyle abutment surface respectively.

During CT-less knee surgery, only certain portions of the femur can be digitized in order to determine essential information. For example, the longitudinal mechanical axis of the femur can be determined, either with or without digitization. In one embodiment, only the most distal portion of the femur's articular surfaces are digitized. The most distal portion of the femur's articular surface (i.e. on the condyles) is particularly important when it is being used to reference specific bone cuts. Alternately, however, the femur can be fully "constructed" by CAS system 10 such that the bone model is as accurate as possible to the anatomy of the patient's bone. While several techniques exist to do this, this can be done using surface model reconstruction, which allows the user to digitize small surfaces instead of points only. When each digitized surface has been registered, an approximate model is displayed on an output device of the CAS system, such as the display device 14. Using this method, the computer femur model is thus formed as a mosaic of digitized surfaces. This reconstruction is done in real time, intra-operatively. Regardless of which of these techniques is employed, a digitizing pointer, or registration tool, is commonly used to acquire several points and/or larger surfaces on the femur, such that these surfaces digitized to form the bone model, which is therefore registered (i.e. the location of the surfaces on the actual bone are matched to the bone model created in the CAS system). During this process, the longitudinal mechanical axis of the femur is also preferably determined. The longitudinal mechanical axis of the femur generally begins at the center of the femoral head (i.e. at the proximal end of the femur), extends the length of the femur, and passes through the center of the inter-condylar notch of the femur. The present invention relates particularly to the digitization of the condyles of the femur, and more particularly with determining a point on the condyles which is the most distally disposed of the femur.

Figure 2A:
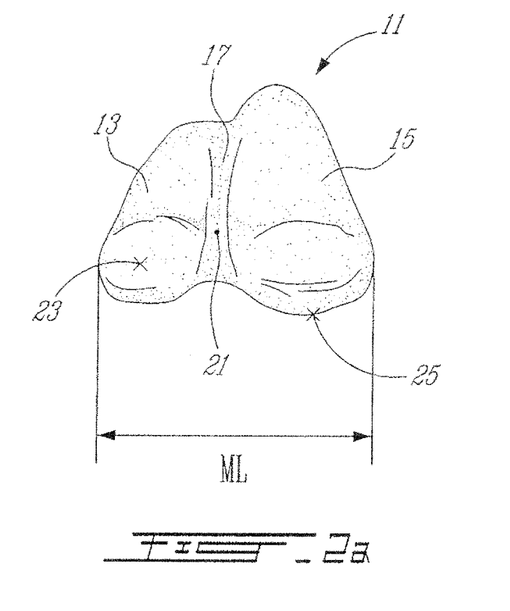
FIG. 2a is a distal end view of a femur.
Figure 2B:
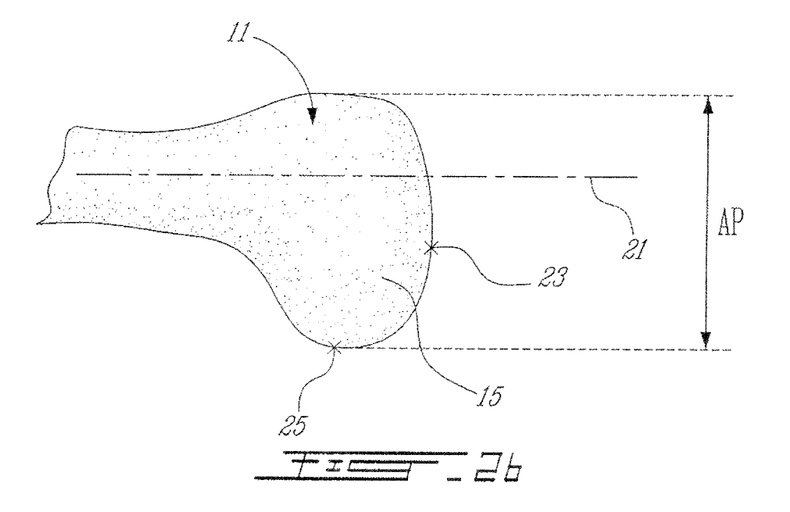

Referring to FIGS. 2a and 2b, a partial portion of the distal end of a femur bone 11 is shown, including a medial condyle 13, a lateral condyle 15 and an inter-condylar notch therebetween. The pre-determined longitudinally extending mechanical axis 21 is also depicted. As the two condyles 13,15 are typically not the same size or shape, even in healthy knees, one of the two condyles (often, but not necessarily, the medial condyle 13) will have a point 23 thereon which is the most distal point on the femoral condyles relative. The present invention permits the determination of this most distal point 23. This point is important, as the CAS system can then measure s from this point to a desired cutting plane 42 (see FIG. 4), in a direction substantially perpendicularly to the cutting plane. Similarly, one of two condyles (often, but not necessarily, the lateral condyle 15) will have a point 25 thereon which is the most posterior of the femoral condyles. The digitizer 20 and CAS system 10 permit the coordinates of at least the most distal of the two points 23 to be determined in a rapid, accurate and user friendly way, as will be described in further detail below. The most posterior of the points 25 can also be similarly determined. In TKR surgery, it is necessary to be able to determine the distal-most point 23 on the condyles 13,15 of the femur 11, such as to accurately calculate the necessary resection distance between this point and the plane through which the resection cut will be made. This is best seen in FIG. 4, described below.

Figure 3:
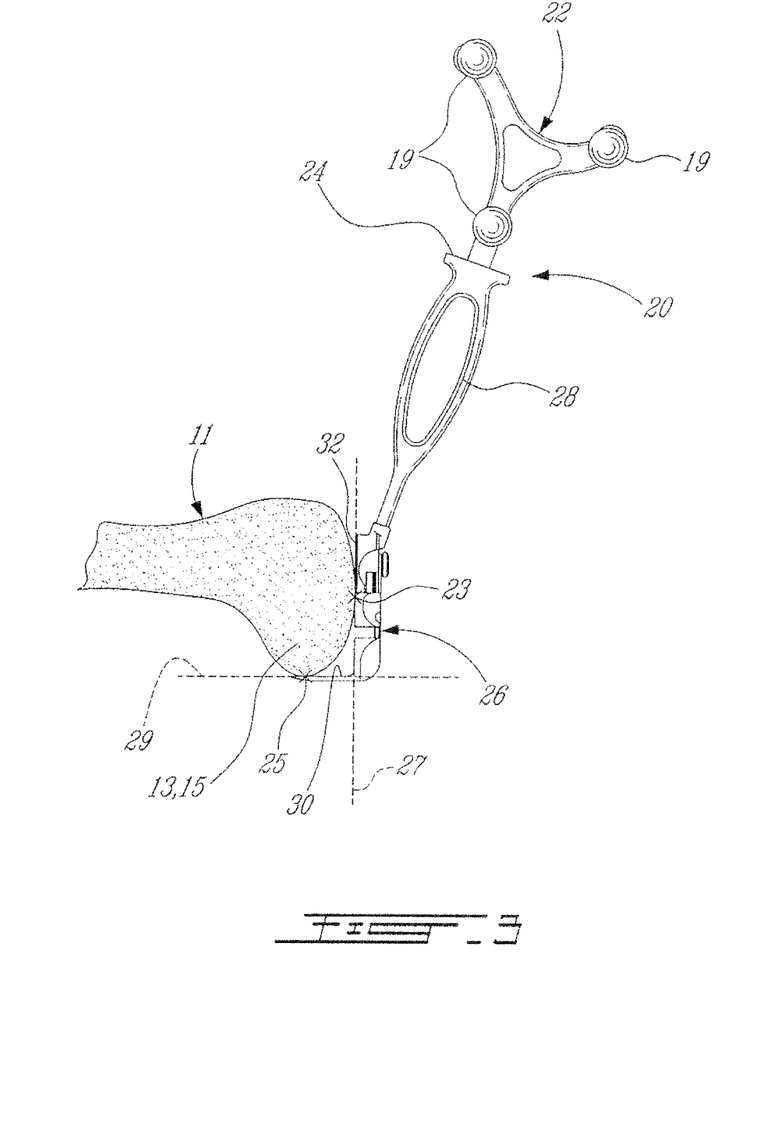
FIG. 3 is a lateral side view of the femur of FIG. 2a the condyle digitizer of FIG. 1 abutted thereagainst.
Figure 4:
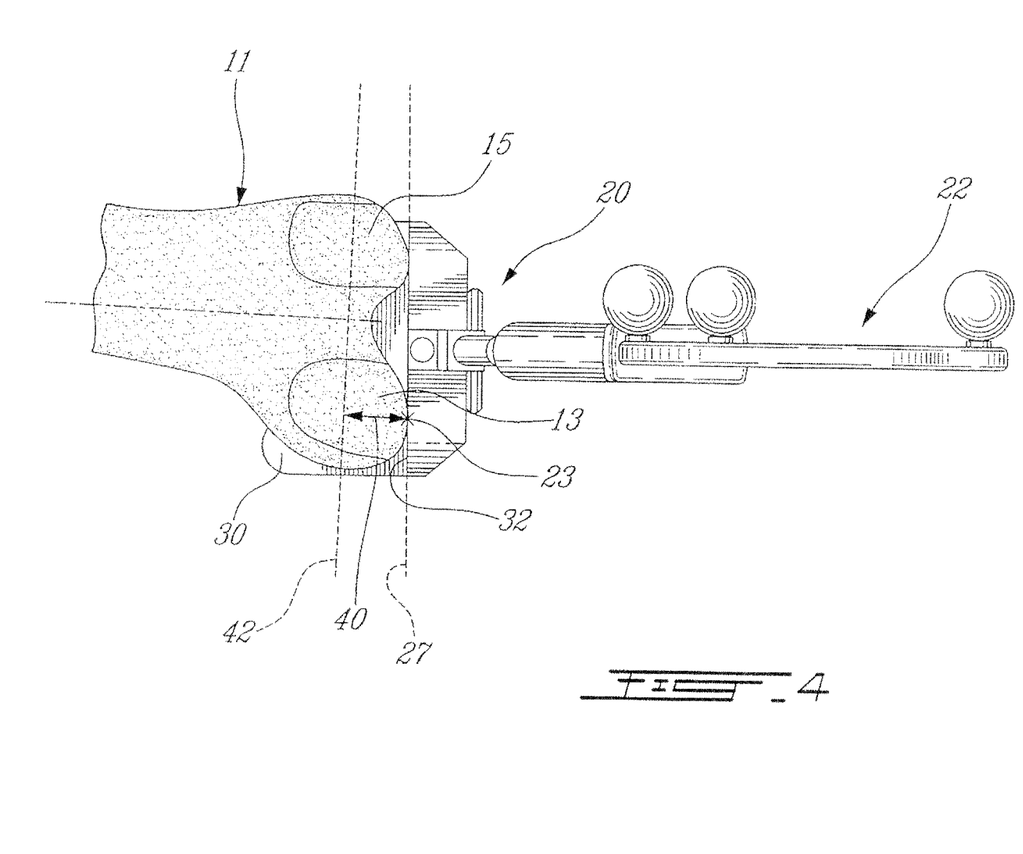
FIG. 4 is an anterior view of FIG. 3.

Referring to FIG. 3 and FIG. 4, the condyle digitizer 20 is shown in use, abutted against the condyles 13, 15 of the femur 11. More specifically, the posterior condyle abutment surface 30 of the digitizer 20 is abutted against the most posterior surfaces of the condyles, and the distal condyle abutment surface 32 is abutted against the distal surfaces of the two condyles. The planar abutment surface 30 intersects the planar abutment surface 32 perpendicularl, thereby defining intersecting first and second planes 29, 27 which also intersect one another perpendicularly. More specifically, the planar abutment surface 30 of the digitizer 20 defines a posterior plane 29 within which the most posterior point 25 of the condyles lies, and the planar abutment surface 32 of the digitizer 20 defines a distal plane 27 within which the most distal point 23 of the condyles lies. As the position and orientation of each of these two planes 27, 29 is known, due to their fixed position relative to the tracking member 22 fixed in place on the digitizer 20, once the two abutment surfaces 30 and 32 of the digitizer 20 have been abutted against their respective condyle surfaces, the CAS system 10 is thus able to identify the distal plane 27 and the posterior plane 29 of the condyles 13, 15 of the femur 11.

When the surfaces 32 and 30 of the digitizing tool 20 are abutted directly against the corresponding surfaces of the condyles, thereby defining the digitized distal and posterior planes 27 and 29 respectively, the CAS system 10 then uses a calculation module programmed therein to determine where on each of these two planes is positioned the most-distal point 23 and/or the most posterior point 25, respectively. I.e., the CAS system 10 is then able, in the manner described below, to determine both the Medial-lateral (ML) coordinate and the Anterior-Posterior (AP) coordinate of one or both of these points. Although in FIG. 3 the digitizer is depicted as being positioned such that the surface 32 thereof (and therefore the plane 27 also) is oriented substantially vertically, the surgeon may alternately orient the digitizer 20 as desired or required, for example such that the surface 32 is positioned at an angle corresponding to the flexion angle of the knee joint or such that the plane 27 of the surface 32 is positioned substantially parallel to a desired resection cutting plane 42, as shown in FIG. 4. In the case that the surface 32 is positioned at an angle corresponding to the flexion angle of the joint, and with reference to the drawing in FIG. 3 showing a lateral side view, this would mean that the surface 32 is inclined clockwise. In this case, the AP coordinate of the most distal point 23 need not be determined by the method described below, as it is then already known and/or determined by the system because the plane 27 is orientated at the flexion angle and therefore the contact point of the surface 32 with the condyles will occur, when disposed in this position, at the most distal location in the AP direction. As such, only the ML direction coordinates of this point need then be determined by the system.

Although this process is described herein with reference to the distal-most point 23 of the femur 11, one skilled in the art will appreciate that a similar method and technique can be used to similarly determine the most posterior point 25 if necessary.

Alternately, the digitizer 20 is provided with a laser marked line on at least the surface 32, which the surgeon can use to line up with a selected most distal point of either condyle in order to digitize this most distal point. As the exact position of this laser marked reference line on the surface 32 is known relative to the tracker 22 of the digitizer 20, the system can thus determine the location of the distal-most point on the condyles when aligned in a medial-lateral direction with this line and abutted against the surface 32. Therefore, while the surgeon positions the digitizer 20 (with the surfaces 30 and 32 abutted against their respective condyle faces) such that the distal plane surface 32 thereof is disposed at the desired angle (such as aligned approximately at the predetermined flexion angle of the knee joint or substantially parallel to the resection cutting plane), he or she then visually aligns in a medial-lateral direction the laser marked line on the surface 32 with a contact zone of the distal condyle surface against said surface 32. The CAS system 10 can then measure the distance between the resection cutting plane 42 and the digitalized line on the surface 32 (the line and the cutting plane 42 being approximately parallel to each other), thus permitting the determination by the CAS system of the ML coordinate of the distal point 23 of the femur. Therefore, when such a reference line is provided on the surface 32 (permitting the system to determine the ML coordinate of the distal point 23), and the above-described method is employed with respect to positioning the surface 32 when acquiring points on the condyles using the digitizer 20 (thus permitting the CAS system to determine the AP coordinate of the distal point 23), the CAS system is able to determine the complete coordinates of the location of the distal-most point 23 on the condyles of the patient's femur.

When the surgeon is positioning the surface 32 in abutment against the condyles, this may be done either with both condyles abutting the surface 32, or alternately with a single condyle (preferably, the visually most distally extending one) abutting the surface 32, while the surgeon orients the digitizer 20 such that the plane 27 of the surface 32 is substantially parallel to a desired resection cutting plane 42 (see FIG. 4).

As discussed in the background section above, when a traditional pointer is used by the surgeon to acquire points on the condyle surfaces such as to digitize their surfaces, identifying the most-distal point on the two condyles can be error-prone. Some reasons for this include the fact that the sharp tip of the digitizing pointer can unintentionally pierce cartilage and other bone and/or tissue on the condyle surfaces, resulting in calculation errors. Additionally, particularly when using a traditional digitizing pointer, for certain bone structures it can be difficult for the surgeon to visually identify exactly which region is in fact the most distal point, such that digitized points can be acquired therearound. In contrast, when using the flat planar surfaces of the digitizer 20 of the present invention, it is much easier for the surgeon to visually appreciate the most distal point on the femoral condyle.

The CAS system 10 of the present invention, in an alternate embodiment, also includes an estimation module which, given a general size envelope of the femoral condyles, can determine with relatively good accuracy where on the known distal plane 27 the most-distal point 23 is located. This estimation module includes a database, which is pre-stored in the memory of CAS system's computer 12, containing data obtained from a sample study of patients, said data including the exact experimentally measured coordinates of femur condyles, including the ML and AP dimensions, and the measured location of the most distal point thereon. While general differences will occur between patients having different sized knees, average values given a good population size are believed to be reasonably reliable. A most commonly employed implant size of a given manufacturer in a specific population can be used as a reference frame, for example. Therefore, using averaged values from the database for the coordinates of the most distal point on the condyles, in conjunction with the known distal plane 27, permits the CAS system 10 to determine an expected location for the most distal point 23 on the femur 11 undergoing surgery.

If the laser marking on the tool's distal surface 32 is used, as described above, then the CAS system need not use this particular estimation module and the pre-stored database to determine an estimated most-distal point. When the laser marking method is used, an accurate line identifying the most-distal point is already known. Using this line and its known distance from the surface 32, three points can be defined on this laser-marked line which are then fed into the CAS system's computing algorithm to determine the location in space, and on the femur, of the most-distal point on the femur from which cut measurements can be made.

Alternately, the database values for the location of the distal point can be classified into datasets based roughly on the knee size (using a given implant sizing number as a group classifier, for example). For example, once the surgeon has determined the appropriate femur implant size, this data is intra-operatively inputted into the CAS system 10, either with or without prompting thereby. The CAS system then uses this info to select the corresponding dataset within the database of measured femur coordinates. This data includes both the Medial-Lateral (ML) coordinate of the most distal point on each of the condyles measured for the database and the Anterior-Posterior (AP) coordinate of each same distal point.

The CAS system 10 will then use the calculated average values for the coordinates of the most distal point on similar condyles, and then will match this information with that of the known distal plane 27 to itself determine a calculated distal point 23 thereon which most likely represents the true distal point of the femur 11. As best seen in FIG. 4, from this most-distal point 23, the CAS system 10 can then calculate a necessary resection distance 40 proximally inward therefrom. This resection distance 40 is thus defined based on the determined location of the resection cut plane 42 through which the femur will be cut by the surgeon to resect the predetermined amount required to install the chosen implant in place on the end of the femur. This resection distance 40 will correspond to the type and size of implant being used. Although the resection cut plane 42 is preferably approximately perpendicular to the longitudinal mechanical axis 21 of the femur as shown in FIG. 4, and therefore not parallel to the distal plane 27, it can alternately be parallel to the distal plane 27. Ideally, the distal resection cut is made substantially perpendicular to the mechanical axis. The minimum resection level is chosen by the surgeon such that the damaged portion of the bone is removed, without removing more than is judged necessary, and such that the chosen implant can be installed in place on the femur.

Several other methods can also be used to determine and provide the CAS system 10 with the general full-scale dimensions (i.e. the full Medial-Lateral (ML) measurement and the full Anterior-Posterior (AP) measurement—see FIGS. 2a-2b) of the femoral condyles 13,15, from which the CAS system 10 is capable of determining, as described above, an approximate position of the most distal point 23 of the femur within the known distal plane 27. The overall size envelope (i.e. the total ML and AP measurements) of the femoral condyles 13,15 of the femur 11 can also be determined, rather than using the averaged values of the measured population used to build the database described above, using either one (or both) of the following alternate methods.

Figure 5:
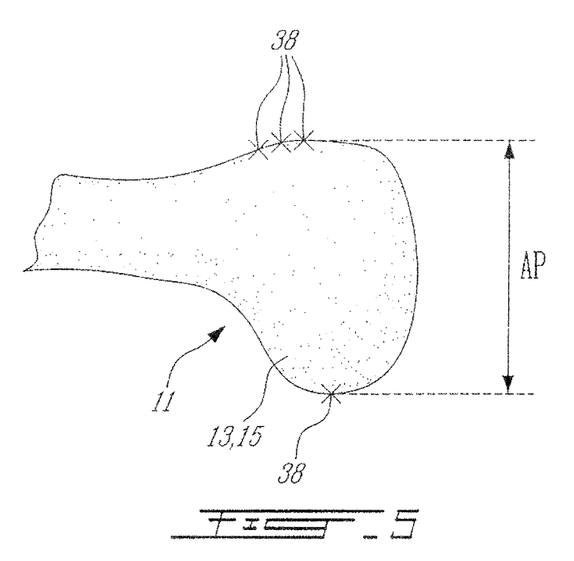

As shown in FIG. 5, the total AP and ML measurements of the femur 11 can be determined by the CAS system's software, by manually digitizing several individual points on both the anterior and posterior surfaces of the femur's condyles 13,15, such that the CAS system 10 can then calculate, based on these points 38, the AP distance of the femur 11. The CAS system 10 can then use this measured dimension of the femur 11 to search the database for similarly sized femurs, and employ the ML and AP coordinates of the most distal points of similarly sized femurs from the database to associate with the known distal plane 27, such that a calculated distal point 23 on this plane 27 is determined by the system to approximate the true most-distal point on the measured femur. Rather than measuring the AP distance of the femur 11 intra-operatively by digitizing points 38 thereon, in another alternate method pre-operatively taken images (such as an x-ray for example) are evaluated to associate a template size, such as one corresponding to implant size for example, which can then be imputed in the CAS system, and then determines the approximate most distal point 23 using the database values as described above. This evaluation may include actual measurement of the x-ray images, or mere qualitative evaluation by the surgeon to determine appropriate implant size, and thus subset of database values used to determine the distal-most point 23 on the distal plane 27. While these methods are proposed and thus preferably used, either alone or in combination, to determine these dimensions, one skilled in the art will appreciate that other means of determining the full scale ML and AP dimensions of the patient's femoral condyles are of course also possible.

Figure 6:
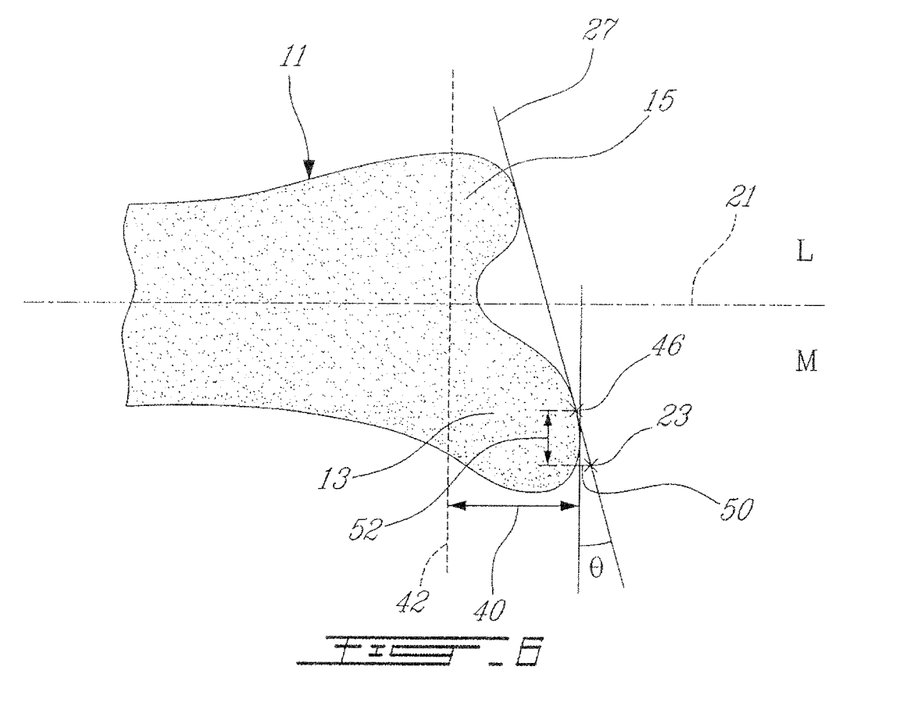
FIG. 6 is an anterior view of the femur of FIG. 2a, showing an approximation of possible calculation error when using the method of the present invention to calculate the location of a distal point on the femoral condyle.

While the determination by the CAS system 10 of the location of the most distal point 23 in the distal plane 27 is an approximation, calculated using averaged literate or measured values, the possible error in this calculation (i.e. between a true most distal point on a femur's condyles and the theoretic or calculated one determined by the CAS system as described above) is relatively small. In fact, this error is believed to be much less than current errors in measurement which occur due to the problems described above with respect to the prior art techniques. For example, referring to FIG. 6, a case in which the predetermined resection distance 40 required is 10 mm and the femur's natural varus-valgus angle θ is 10 degrees is depicted, for the purposes of calculating a worst case resection error value when the above-described method is used by the CAS system 10 to approximate the locations of the most-distal point 23 on the femur. The point 23 on the known distal plane represents the location of the point calculated by the system to be the most distal point on the condyles of the femur in question. The point 46 represents the true most-distal point. Given that the size of most femoral condyles, while varying from person to person, does not vary by huge amounts, assuming for the present calculation an error distance 52 (i.e. between the true distal point 46 and the distal point 23 calculated by the CAS system 10) in the ML direction to be 5 mm. By Pythagoras's theorem, the resection distance error 50 is equal to the ML error distance 52 of 5 mm multiplied by the sine of the varus-valgus angle θ of 10 degrees. This gives a possible resection error distance 50 of less than 1 mm, which given this is a worst case scenario, is believed to be very acceptable.

Although the present invention is preferably used with a CT-free CAS system 10, it is nevertheless to be understood that the step of performing a digitization or registration of the bone element, as described above, comprises all means of relating the actual bone element to a corresponding model or image of the same bone element. Those skilled in the art will appreciate that there are a plurality of ways of creating such a model or image of the bone element, and of relating or matching the actual bone element to the model or image thereof. All similarly suitable methods of generating a computerized model or displaying image of the bone element, and of relating or matching the position and orientation of the actual bone element thereto, will be understood herein to be included in the process of performing a registration of the bone element.

All surfaces of the digitizer 20 can be easily cleaned. Particularly, all surfaces can be sufficiently exposed such that thorough pressure cleaning is possible. The ability to sterilize all surfaces of the device by pressure cleaning and autoclaving is important to ensure that all potentially contaminating biological matter can be safely removed. Such potentially dangerous contaminating biological matter can include unwanted bacteria and proteins, which can cause infections or diseases.

Although throughout this specification the present invention is generally described with regard to its use in total knee replacement (TKR) surgery, it is to be understood that the present invention can be similarly used in conjunction with all types of orthopedic knee surgery, for example partial knee replacement, knee repair operations, and the like. Further, although the present invention is described herein principally with regard to determining a most-distal point on the femur, it is to be understood that the same method and system described can also be used to determine a most proximal end point on a tibia. Further still, although the two perpendicular abutting surfaces of the condyle digitizer described herein are used in the embodiment described and depicted to determine points on the distal surface and/or the posterior surface of the femoral condyles, one skilled in the art will appreciate that by inverting the tool relative to the femur the same condyle digitizer of the present invention can be used, if necessary, to determine an anterior point on the anterior surface of the condyles.

The embodiments of the invention described above are intended to be exemplary only. The scope of the invention is therefore intended to be limited solely by the scope of the appended claims.

The invention claimed is:

1. A computer assisted surgery system for conducting orthopedic surgery on a knee joint, the knee joint including a femur defining a longitudinal mechanical axis and having condyles on the distal end thereof, the system comprising:
   a condyle digitizer including a posterior condyle abutment surface defining a first plane and a distal condyle abutment surface intersecting perpendicularly the posterior condyle abutment surface and defining a second plane perpendicular to said first plane, and at least one trackable member which is locatable and trackable in three dimensional space by the computer assisted surgery system, thereby defining at least an orientation of the condyle digitizer in real time; and
   a computer in communication with the condyle digitizer, the computer being operable to determine a most remote reference point of the femur lying within at least one of said first and second planes when said condyle digitizer is abutted directly against the condyles of the femur such that the posterior condyle abutment surface directly abuts a posterior side of the condyles and the distal condyle abutment surface directly abuts a distal side of the condyles.

2. The computer assisted surgery system as defined in claim 1, further comprising a display device which graphically indicates a location of the determined most remote reference point on the femur.

3. A computer assisted surgery system for orthopedic knee surgery comprising:
   a digitizer having perpendicularly intersecting first and second planar surfaces respectively directly abuttable against posterior and distal surfaces of condyles of a femur;
   means for determining at least an orientation of said first and second planar surfaces relative to the femur; and
   means for determining the location of a reference point in a digitized plane defined on at least one of said first and second planar surfaces when abutted directly against the respective proximal and distal surfaces of the condyles, said reference point being a most remote point of the femur within said digitized plane.

4. The system as defined in claim 3, further comprising means for determining and indicating a location of a distal resection cut calculated by the computer assisted surgery system based on a resection distance measured from said reference point.

5. The computer assisted surgery system as defined in claim 1, wherein the posterior condyle abutment surface or the distal condyle abutment surface of the condyle digitizer are disposed at a predetermined angle relative to the knee joint.

6. The computer assisted surgery system as defined in claim 5, wherein said predetermined angle includes one of a first angle substantially parallel to that of a desired resection cut and a second angle substantially parallel to a flexion angle of the knee joint of said femur.

7. The computer assisted surgery system as defined in claim 1, wherein the computer further comprises a database of coordinates of measured points on femoral condyles, and is operable to determine an average value of a subset of said database to calculate the most remote reference point.

8. The computer assisted surgery system as defined in claim 2, wherein the computer is operable to determine a location of a distal resection cut in the femur by calculating a selected resection distance away from the most remote reference point.

9. The computer assisted surgery system as defined in claim 8, wherein the display device depicts at least the location of the distal resection cut on the femur.

10. The computer assisted surgery system as defined in claim 1, wherein the computer assisted surgery system determines and displays on a display device position and orientation of the condyle digitizer relative to the femur.

11. The computer assisted surgery system as defined in claim 1, wherein a laser marked alignment line is disposed on at least one of the posterior condyle abutment surface and the distal condyle abutment surface of the condyle digitizer.

12. A computer assisted surgery system for orthopedic knee surgery comprising:
a digitizer having perpendicularly intersecting first and second planar surfaces respectively directly abuttable against posterior and distal surfaces of condyles of a femur; and
a computer in communication with the condyle digitizer, the computer being operable to determine at least orientation of said first and second planar surfaces relative to the femur, and to determine the location of a reference point in a digitized plane defined by at least one of said first and second planar surfaces when abutted directly against the respective proximal and distal surfaces of the condyles, said reference point being a most remote point of the femur within said digitized plane.

13. The computer assisted surgery system as defined in claim 12, wherein the computer is operable to determine a location of a distal resection cut in the femur by calculating a selected resection distance away from the most remote point.

14. The computer assisted surgery system as defined in claim 13, further comprising a display device in communication with the computer which depicts at least the location of the distal resection cut on the femur.

15. The computer assisted surgery system as defined in claim 1, wherein the computer assisted surgery system determines and displays on a display device position and orientation of the digitizer relative to the femur.

16. The system as defined in claim 13, further comprising a display device in communication with the computer, the determined location of the distal resection cut in the femur being depicted on said display device.

* * * * *